United States Patent
Erdelmeier et al.

(10) Patent No.: US 7,022,317 B2
(45) Date of Patent: Apr. 4, 2006

(54) HETEROCYCLIC DERIVATIVES OF 2-OXOTHIAZOLIDINE-4-CARBOXYLIC ACID, AND USE AS ACTIVE PHOTOPROTECTIVE AGENTS

(75) Inventors: Irène Erdelmeier, Paris (FR); Karine Lucet-Levannier, Reuil-Malmaison (FR)

(73) Assignee: L'Oreal, (FR)

( * ) Notice: Subject to any disclaimer, the term of this patent is extended or adjusted under 35 U.S.C. 154(b) by 130 days.

(21) Appl. No.: 10/830,924

(22) Filed: Apr. 23, 2004

(65) Prior Publication Data

US 2005/0129635 A1    Jun. 16, 2005

Related U.S. Application Data

(60) Provisional application No. 60/472,766, filed on May 22, 2003.

(30) Foreign Application Priority Data

Apr. 25, 2003   (FR) .................................. 03 05118

(51) Int. Cl.
*A61K 7/42* (2006.01)
*A61K 31/4985* (2006.01)
*A61K 31/5365* (2006.01)
*C07D 513/04* (2006.01)

(52) U.S. Cl. ............... 424/59; 514/221; 514/230.5; 514/249; 540/503; 544/105; 544/350

(58) Field of Classification Search ............... 540/503; 544/105, 350; 514/221, 230.5, 249; 424/59
See application file for complete search history.

(56) References Cited

U.S. PATENT DOCUMENTS 6,004,543 A * 12/1999 Galey ........................ 424/62
6,337,077 B1 * 1/2002 Chevalier et al. ........... 424/401

FOREIGN PATENT DOCUMENTS

| EP | 0 465 191 | 1/1992 |
|----|-----------|--------|
| EP | 0 583 863 | 2/1994 |
| EP | 0 650 725 | 5/1995 |
| EP | 0 655 245 | 5/1995 |

* cited by examiner

*Primary Examiner*—Fiona T. Powers
(74) *Attorney, Agent, or Firm*—Lerner, David, Littenberg, Krumholz & Mentlik, LLP

(57) ABSTRACT

The present invention relates to novel heterocyclic derivatives of 2-oxothiazolidine-4-carboxylic acid, to a process for synthesizing them and to compositions containing them.

The invention also relates to the use of at least one heterocyclic derivative of 2-oxathiazolidine-4-carboxylic acid in a composition or for the manufacture of a composition, the said derivative or the said composition being intended to induce active photoprotection of the skin, advantageously to prepare the skin to receive sunlight and/or to protect the skin and other epidermal growths during or after exposure to UV.

Another subject of the invention also relates to a cosmetic process for treating the skin by oral administration or topical administration to the skin of a cosmetic composition as defined above.

31 Claims, 1 Drawing Sheet

HETEROCYCLIC DERIVATIVES OF 2-OXOTHIAZOLIDINE-4-CARBOXYLIC ACID, AND USE AS ACTIVE PHOTOPROTECTIVE AGENTS

CROSS-REFERENCE TO RELATED APPLICATIONS

The present application claims the benefit of French Patent Application No. 0305118, filed Apr. 25, 2003; and U.S. Provisional Patent Application No. 60/472,766, filed May 22, 2003, the disclosures of which are incorporated by reference herein.

BACKGROUND OF THE INVENTION

In order to protect the skin against the harmful effects of sunlight, it is well known to provide artificial photoprotection by the topical cutaneous application of agents that prevent the action of UV in two ways:
by absorbing the energy supplied by the photons; these are standard UVA-active and/or UVB-active organic and/or mineral sunscreens;
by scattering the light using a physical sunblock, for instance titanium dioxide. "Total sunblock" creams generally contain such a product plus a chemical screening agent.

Antioxidants such as vitamin E, carotenoids or glutathione, which may be of value in reducing the effects of cellular oxidative stress, may also be provided. These agents induce active photoprotection by stimulating the natural defence systems of the skin cells against the damage induced by UV irradiation.

The use of 2-oxothiazolidine-4-carboxylic acid has already been the subject of numerous studies and patents, especially with the aim of protecting the body against various types of stress. Thus, it is known from document U.S. Pat. No. 5,208,249 (Clintec) that 2-oxothiazolidine-4-carboxylic acid and its esters are capable of stimulating glutathione synthesis in certain cells of the human body. Glutathione, which is found in all eukaryotic cells, is a tripeptide composed of the following three amino acids: glutamic acid, cysteine and glycine. Glutathione is especially known to participate in protecting cells against various types of damage, such as that caused by free radicals (U.S. Pat. No. 5,208,249) and to play a central role in the antioxidant defence systems against free radicals and toxic compounds of endogenous and exogenous origin (J. Med. Chem., 1999, Vol. 42, No. 23, pp. 4733–4740).

In addition, it is known practice from document EP 0 655 245 (Free Radical Science) to use a composition containing 2-oxothiazolidine-4-carboxylic acid or its esters to delay the ageing process in mammals, by maintaining intracellular glutathione levels at an amount that is sufficient to prevent the oxidative damage caused by free radicals on cells.

It nevertheless remains that the desire to protect the skin and other epidermal growths against oxidative and photooxidative stress in order to maintain or improve the appearance of an individual's skin still leads to the incessant search for novel agents that are effective for protecting the skin and other epidermal growths, the said agents moreover needing to be well metabolized and able to be formulated in compositions, especially cosmetic compositions.

A process for synthesizing a heterocyclic derivative of formula (II) has indeed been reported in the prior art (Bull. Chem. Soc. Jpn., 1964, 37 (2), pp. 242–244), but this derivative is not described as an agent for stimulating the intracellular synthesis of glutathione.

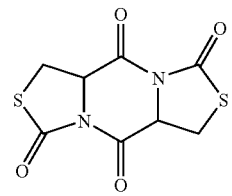

(II)

SUMMARY OF THE INVENTION

The present invention relates to novel heterocyclic derivatives of 2-oxothiazolidine-4-carboxylic acid, and in particular those of Formula (I) to a process for synthesizing them and to compositions containing them.

The invention also relates to the use of at least one heterocyclic derivative of 2-oxathiazolidine-4-carboxylic acid as disclosed herein in a composition or for the manufacture of a composition, the said derivative or the said composition being intended to induce active photoprotection of the skin, advantageously to prepare the skin to receive sunlight and/or to protect the skin and other epidermal growths during or after exposure to UV.

Another subject of the invention also relates to a cosmetic process for treating the skin by oral administration or topical administration to the skin of a cosmetic composition as defined above.

DETAILED DESCRIPTION

Figure 1:
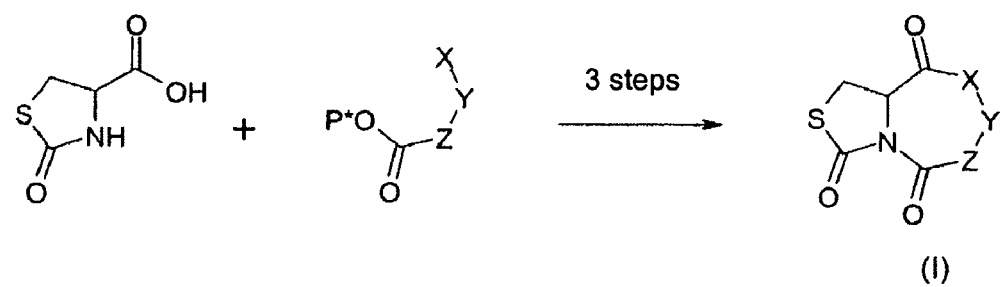
FIG. 1 illustrates a reaction pathway for producing at least some of the derivatives of Formula (I).

The Applicant has now discovered, surprisingly and unexpectedly, novel heterocyclic derivatives of 2-oxothiazolidine-4-carboxylic acid which are agents capable of inducing active photoprotection of the skin, by means of stimulating the intracellular synthesis of glutathione, which makes it possible to prepare the skin to receive sunlight and/or to protect the skin and other epidermal growths during or after exposure to UV.

The present invention is based on the Applicant's observation that the novel heterocyclic derivatives of 2-oxothiazolidine-4-carboxylic acid of formula (I) as defined below are excellent agents for stimulating the intracellular synthesis of glutathione.

One subject of the invention is thus novel 2-oxothiazolidine-4-carboxylic acid derivatives corresponding to formula (I) below:

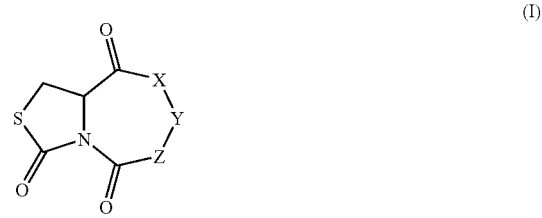

(I)

in which:

X represents an oxygen atom or a radical NR";

R" represents a linear, cyclic or branched alkyl radical containing from 1 to 12 carbon atoms and advantageously from 1 to 6 carbon atoms, which is optionally substituted, preferably with at least one —COOH, —NH$_2$, —OH and/or —SH radical;

Y represents a group (CH$_2$)$_n$;

z represents a group (CRR')

n is an integer chosen from 0, 1, 2 and 3, preferably 0 or 1, and advantageously n is equal to 0;

R and R', which may be identical or different, represent:
a hydrogen atom;
an —Si—(CH$_3$)$_3$, —Si (CH$_3$)$_2$—OH, Si—(CH$_3$)$_2$-OEt, —Si—(CH$_3$)$_2$—O—CH$_2$—Ph or —Si—(iPr)$_2$-OEt radical;
a halogen;
an alkyl radical as defined above;
an optionally substituted aryl radical;
an optionally substituted arylalkyl radical; it being understood that when X represents a radical NR", R" and R' taken together can form, with the 2 atoms bearing them, a heterocycle containing 4, 5 or 6 carbon atoms and preferably 4 carbon atoms;
or Y and Z each represent a carbon atom and together form an aromatic heterocycle or ring containing 5, 6 or 7 carbon atoms and preferably 6 carbon atoms, the said ring or heterocycle being optionally substituted; the optical and/or geometrical isomers thereof, alone or as a mixture in all proportions, and also the physiologically acceptable salts thereof.

The invention thus also relates to the optical and/or geometrical isomers of the derivatives of formula (I), alone or as a mixture in all proportions, and also the physiologically acceptable salts of these derivatives.

Salts of the derivative of formula (I) that may be mentioned include the salts obtained by addition of the derivative of formula (I) with a mineral acid chosen especially from hydrochloric acid, sulphuric acid, nitric acid, carbonic acid and phosphoric acid, or with an organic acid chosen in particular from succinic acid, fumaric acid, lactic acid, glycolic acid, citric acid, gluconic acid, salicylic acid and tartaric acid.

For the purposes of the invention, the term "aryl radical" is understood as being a 5- or 6-membered aromatic ring or a 5- or 6-membered aromatic heterocycle. An aryl radical that is particularly preferred according to the invention is the phenyl radical.

According to the invention, the term "arylalkyl radical" preferably means alkyl-aryl radicals containing from 6 to 12 carbon atoms, in which definition the term aryl is understood as being a 5- or 6-membered aromatic ring or a 5- or 6-membered aromatic heterocycle. Preferably, according to the invention, the arylalkyl radical is of C$_7$–C$_{10}$. An arylalkyl radical that is particularly preferred according to the invention is the benzyl radical.

The terms "substituted aryl radical" and "substituted arylalkyl radical" mean a radical in which the aromatic portion is substituted with at least one group chosen from a hydroxyl group (—OH), a cyano group (—CN), a trifluoromethyl group (—CF$_3$), a methoxy radical (—OCH$_3$) or a halogen atom. The halogen atom may be chosen from chlorine, bromine, fluorine and iodine.

A substituted aryl radical that is preferred according to the invention is a phenyl radical substituted with an alkyl radical, a hydroxyl group or a methoxy radical.

A substituted arylalkyl radical that is preferred according to the invention is a benzyl radical substituted with at least one group chosen from an alkyl radical, a hydroxyl group and a methoxy radical.

Preferably, according to the invention, the alkyl radical is of C$_1$–C$_4$ and is chosen from methyl, ethyl, propyl, isopropyl, butyl, isobutyl and tert-butyl radicals and more particularly methyl or ethyl radicals.

According to one preferred embodiment of the invention, the derivative of formula (I) is such that at least one of the following conditions, and preferably all of these conditions, are satisfied:

X represents an oxygen atom or a radical NR";

n is equal to 0;

Z represents a group (CRR');

R and R", which may be identical or different, represent a hydrogen atom, an alkyl radical as defined above or a cycloalkyl;

R' represents a hydrogen atom, a phenyl radical, a benzyl radical or the side chain of an amino acid, preferably chosen from that of alanine, isoleucine, leucine, methionine, phenylalanine, tryptophan, valine, asparagine, cysteine, glutamine, glycine, serine, threonine, aspartic acid, glutamic acid, arginine, histidine and lysine;

it being understood that R" and R taken together can form, with the two atoms bearing them, the side chain of proline, or Y and Z each represent a carbon atom and together form an optionally substituted aromatic ring containing 6 carbon atoms.

The compounds that are preferred according to the invention are chosen from the following compounds:
tetrahydrothiazolo[3,4-a]pyrazine-3,5,8-trione;
6-methyltetrahydro[1,3]thiazolo[3,4-a]pyrazine-3,5,8-trione;
6-ethyltetrahydro[1,3]thiazolo[3,4-a]pyrazine-3,5,8-trione;
6-propyltetrahydro[1,3]thiazolo[3,4-a]pyrazine-3,5,8-trione;
6-iso-propyltetrahydro[1,3]thiazolo[3,4-a]pyrazine-3,5,8-trione;
6-propyltetrahydro[1,3]thiazolo[3,4-a]pyrazine-3,5,8-trione;
6-[1-methylpropyl]tetrahydro[1,3]thiazolo[3,4-a]-pyrazine-3,5,8-trione;
6-isobutyltetrahydro[1,3]thiazolo[3,4-a]pyrazine-3,5,8-trione;
6-phenyltetrahydro[1,3]thiazolo[3,4-a]pyrazine-3,5,8-trione;
6-benzyltetrahydro[1,3]thiazolo[3,4-a]pyrazine-3,5,8-trione;
6-(methylsulphanyl)ethyltetrahydro[1,3]thiazolo-[3,4-a]pyrazine-3,5,8-trione;
6-(ethylsulphanyl)methyltetrahydro[1,3]thiazolo-[3,4-a]pyrazine-3,5,8-trione;
7-methyltetrahydrotetra[1,3]thiazolo[3,4-a]pyrazine-3,5,8-trione;
7-ethyltetrahydrotetra[1,3]thiazolo[3,4-a]pyrazine-3,5,8-trione;
tetrahydro-1H,5H-pyrrolo[1,2a][1,3]thiazolo[3,4d]-pyrazine-3,5,10(10aH)trione;
3-(3,5,8-trioxohexahydrothiazolo[3,4-a]pyrazin-6-yl)propionic acid;
6-mercaptomethyltetrahydrothiazolo[3,4-a]pyrazine-3,5,8-trione;
7-methyltetrahydrothiazolo[3,4-a]pyrazine-3,5,8-trione;
6,7-dimethyltetrahydro[1,3]thiazolo[3,4-a]pyrazine-3,5,8-trione;

6-ethyl-7-methyltetrahydro[1,3]thiazolo[3,4-a]-pyrazine-3,5,8-trione;
6-propyl-7-methyltetrahydro[1,3]thiazolo[3,4-a]-pyrazine-3,5,8-trione;
6-iso-propyl-7-methyltetrahydro[1,3]thiazolo[3,4-a]pyrazine-3,5,8-trione;
6-propyl-7-methyltetrahydro[1,3]thiazolo[3,4-a]-pyrazine-3,5,8-trione;
6-[1-methylpropyl]-7-methyltetrahydro[1,3]thiazolo-[3,4-a]pyrazine-3,5,8-trione;
6-iso-butyl-7-methyltetrahydro[1,3]thiazolo[3,4-a]-pyrazine-3,5,8-trione;
6-phenyl-7-methyltetrahydro[1,3]thiazolo[3,4-a]-pyrazine-3,5,8-trione,
6-benzyl-7-methyltetrahydro[1,3]thiazolo[3,4-a]-pyrazine-3,5,8-trione;
6-(methylsulphanyl)ethyl-7-methyltetrahydro[1,3]-thiazolo[3,4-a]pyrazine-3,5,8-trione;
6-(ethylsulphanyl)methyl-7-methyltetrahydro[1,3]-thiazolo[3,4-a]pyrazine-3,5,8-trione;
3-(3,5,8-trioxohexahydro-7-methylthiazolo[3,4-a]-pyrazin-6-yl)propionic acid;
6-mercaptomethyl-7-methyltetrahydrothiazolo[3,4-a]-pyrazine-3,5,8-trione;
1H-[1,3]thiazolo[4,3-c]oxazine-3,5,8-[6H,8aH]trione;
1,10a-dihydro-9-oxa-2-thia-3a-azabenzo[f]azulene-3,4,10-trione;
6-octanoyl-1,10a-dihydro-9-oxa-2-thia-3a-azabenzo[f]azulene-3,4,10-trione;
(6-carboxymethyl-3,5,8-trioxotetrahydrothiazolo-[4,3-c][1,4]oxazin-6-yl)acetic acid, the optical and/or geometrical isomers thereof, alone or as a mixture in all proportions, and also the physiologically acceptable salts thereof.

The compounds that are particularly preferred according to the invention are chosen from the following compounds:
1H-[1,3]thiazolo[4,3-c]oxazine-3,5,8-[6H,8aH]trione;
hexahydropyrrolo[1,2-a]thiazolo[3,4-d]pyrazine-3,5,10-trione;
6-benzyltetrahydrothiazolo[3,4-a]pyrazine-3,5,8-trione;
tetrahydrothiazolo[3,4-a]pyrazine-3,5,8-trione;
6-phenyltetrahydrothiazolo[3,4-a]pyrazine-3,5,8-trione, the optical and/or geometrical isomers thereof, alone or as a mixture in all proportions, and also the physiologically acceptable salts thereof.

Thus, another subject of the invention relates to the use of at least one heterocyclic derivative of 2-oxothiazolidine-4-carboxylic acid of Formula (I) as defined above in a composition or for the manufacture of a composition, the said derivative or the said composition being intended to induce active photoprotection of the skin, advantageously to prepare the skin to receive sunlight and/or to protect the skin and other epidermal growths during or after exposure to UV.

The term "other epidermal growths" means, for example, the hair and the nails.

Another subject of the invention also relates to the cosmetic use of at least one compound of formula (I) as defined above, as an agent for stimulating the intracellular synthesis of glutathione and/or for maintaining an intracellular level of glutathione at an amount that is sufficient to prevent the oxidative damage caused by free radicals on cells.

Ageing of the skin results from two distinct and independent processes involving intrinsic or extrinsic factors. Intrinsic or chronobiological ageing corresponds to "normal" or age-related physiological ageing. Extrinsic ageing corresponds to ageing caused generally by the environment and more particularly photoageing due to exposure to sunlight, to light or to any other radiation (EP-A2-0 815 840, Kligman, A. M. et al., Journal of Cutaneous Aging and Cosmetic Dermatology, Vol. 1, No. 1, pp. 5–12 (1988)).

Ageing of the skin which results from the effects of intrinsic or extrinsic factors on the skin is generally reflected by the appearance of wrinkles and fine lines, by yellowing of the skin which develops a wizened appearance accompanied by the appearance of pigmentation marks, by disorganization of the elastin and collagen fibres resulting in a loss of elasticity, suppleness and firmness, and by the appearance of telangiectasias.

By means of stimulating the intracellular synthesis of glutathione and/or by maintaining an intracellular level of glutathione, the derivatives of formula (I) according to the invention make it possible to prevent or reduce the effects on the skin of the intrinsic or extrinsic factors described above.

Advantageously, the invention thus relates to the use of at least one derivative of formula (I) as defined above, in a composition or for the manufacture of a composition, the said derivative or the said composition being intended to combat intrinsic and/or extrinsic ageing of the skin.

In addition, the derivatives of formula (I), advantageously the derivatives for which X represents an oxygen atom as defined above, constitute excellent active agents for promoting desquamation of the skin and/or for stimulating epidermal renewal and make it possible more effectively to combat intrinsic and/or extrinsic ageing of the skin.

Another subject of the invention relates to the use of at least one derivative of formula (I) as defined above in a composition or for the manufacture of a composition, the said derivative or the said composition being intended to promote desquamation of the skin and/or to stimulate epidermal renewal and is advantageously intended to combat intrinsic and/or extrinsic ageing of the skin.

The process for manufacturing the derivatives of formula (I) according to the invention follows the general synthetic scheme presented in FIG. 1 (FIG. 1).

The starting materials are 2-oxothiazolidine-4-carboxylic acid and an amino acid, a hydroxy acid or a halo acid whose acid function is protected (P*).

The starting amino acid is an α, β or γ-amino acid.
The starting hydroxy acid is an α-, β- or γ-hydroxy acid.
The starting halo acid is an α-, β- or γ-halo acid.

The starting amino acid, hydroxy acid or halo acid may be obtained in protected form according to methods conventionally used in organic synthesis that are well known to those skilled in the art, for example those described in the document *Protective Groups in Organic Synthesis*, T. W. Greene, P. G. M. Wuts (Wiley Interscience).

The amino acid, hydroxy acid or halo acid, which is free or in protected form, may also be obtained directly from suppliers.

At least some of the derivatives of formula (I) according to the invention may be obtained according to conventionally used peptide coupling methods that are well known to those skilled in the art, for example those described in document *Peptide Chemistry—A Practical Textbook*, Miklos Bodanszky, 1988 (Springer Verlag).

Thus, another subject of the invention also relates to a process for manufacturing the derivatives of formula (I) as defined above, from L-2-oxothiazolidine-4-carboxylic acid, characterized in that it comprises the following steps:
i) coupling reaction, in the presence of a base, between 2-oxothiazolidine-4-carboxylic acid and an amino acid, a hydroxy acid or a halo acid whose acid function is protected;

ii) reaction of deprotection with an acidic agent of the protected acid function of the product obtained after step i);

iii) intramolecular cyclization reaction of peptide type;

it being understood that step iii) is performed if the intramolecular cyclization does not take place spontaneously in step ii).

According to one preferred embodiment of the invention, the process is such that at least one of the following conditions, and preferably all these conditions, are satisfied:

When the starting material is a halo acid, step i) includes:

placing the 2-oxothiazolidine-4-carboxylic acid in a polar solvent, which is preferably anhydrous, preferably acetonitrile or DMF;

adding at least one organic or mineral base, preferably potassium carbonate, preferably 0.1 to 2 equivalents;

adding a halo acid, preferably a bromo acid, the acid function of which is protected, preferably from 1 to 3 equivalents.

When the starting material is an amino acid or a hydroxy acid, step i) includes:

placing the 2-oxothiazolidine-4-carboxylic acid in a polar solvent, which is preferably anhydrous, preferably acetonitrile;

adding at least one coupling agent, preferably 1 equivalent, and/or an additive to prevent enantiomerization during the coupling, preferably 1 equivalent;

adding an amino acid or a hydroxy acid whose acid function is protected, preferably 1 equivalent, and a base, preferably a tertiary amine, advantageously triethylamine, preferably 1 equivalent. When the amino acid whose acid function is protected is in hydrochloride form, 2 equivalents of base and preferably of triethylamine are used.

An additive is used to prevent enantiomerization during the coupling when the starting amino acid or hydroxy acid are optically pure.

Step ii) includes:

placing the product obtained from step i), preferably 1 equivalent, in an aprotic solvent;

adding an acidic agent, advantageously trifluoroacetic acid, preferably 5 equivalents, advantageously in the presence of a silane, preferably triethylsilane or triisopropylsilane, preferably 1 equivalent.

The products obtained after step ii) may be used directly in step iii) or worked up according to techniques that are well known to those skilled in the art.

Depending on the nature of the intermediate derivatives obtained after step ii), the work-up will be different:

a) if the compound is lipophilic, the product is taken up in an organic solvent and then extracted with saturated aqueous sodium hydrogen carbonate solution. The aqueous phase is subsequently acidified and then taken up in an organic solvent.

b) if the compound is hydrophilic, it is precipitated in an apolar solvent, for example diethyl ether. According to another method, the hydrophilic compound is dissolved in water and then washed with an organic solvent. The aqueous phase is then freeze-dried.

Step iii) includes:

placing the product obtained after step ii), preferably one molar equivalent, in a polar, preferably anhydrous solvent, preferably acetonitrile;

adding at least one coupling agent, preferably one molar equivalent, and/or an additive to prevent enantiomerization during coupling, preferably 1 molar equivalent.

Optionally, an organic base, advantageously a tertiary amine and preferably triethylamine, is added, preferably 1 molar equivalent.

The derivatives of formula (I) obtained after step iii) may be of two types.

a) Case of the derivatives that are stable in protic solvents (water, methanol):

The dry product is taken up in an organic solvent and then washed with water.

After the usual work-up of the organic phase, the dry product is dissolved in a solvent in which the residual coupling agents remain insoluble, and these are removed by filtration.

b) Case of the derivatives that are unstable in protic solvents (water, methanol):

The dry product is purified by column chromatography or by precipitation from an apolar solvent, for example diethyl ether.

The products of formula (I) may be isolated in optically pure form according to methods that are well known to those skilled in the art, for instance HPLC, including reverse-phase HPLC.

A coupling agent that is preferred according to the invention is chosen from DCC (dicyclohexylcarbodiimide) and EDCI (1-(3-dimethylaminopropyl)-3-ethylcarbodiimide, HCl)).

An additive for preventing enantiomerization during coupling, which is preferred according to the invention, is chosen from HOBt (1-hydroxybenzotriazole) and NHS(N-hydroxysuccinimide).

An in-situ activating agent that is preferred according to the invention is HBTU (2-(1H-benzotriazolyl)-1,1,3,3-tetramethyluronium hexafluorophosphate).

According to step i), when the 2-oxothiazolidine-4-carboxylic acid reacts with a hydroxy acid whose acid function is protected, DCC and NHS are used.

According to the invention, when the starting amino acid, hydroxy acid or halo acid used in step i) according to the invention contains an alkyl side chain substituted with at least one —COOH, —$NH_2$, —OH and/or —SH radical, the said radical is protected according to the methods conventionally used in organic synthesis and well known to those skilled in the art, for instance those described in the document *Protective Groups in Organic Synthesis*, T. W. Greene, P. G. M. Wuts (Wiley Interscience).

Advantageously, the —COOH radical present on the side chain is protected with a tert-butyl group; the —$NH_2$ radical present on the side chain is protected with a tBoc (tert-butyloxycarbonyl); the —OH or —SH radical present on the side chain is protected with a tert-butyl or tBoc radical. These —COOH, —$NH_2$, —OH and/or —SH radicals will be deprotected in acidic medium in step ii).

The synthetic process according to the invention may be performed using enantiomerically pure starting materials. The starting 2-oxathiazolidine-4-carboxylic acid is commercially available in racemic form or in L form, and may also be obtained synthetically in D form.

When the derivatives of formula (I) are obtained in the form of a racemic mixture, the various constituent diastereoisomers of this mixture may be separated, for example, by preparative HPLC according to methods that are well known to those skilled in the art.

Another subject of the invention relates to a composition containing, in a physiologically acceptable medium, at least one derivative of formula (I) as defined above.

The amount of derivative(s) of formula (I) that may be used according to the invention obviously depends on the desired effect and may thus vary within a wide range.

To give an order of magnitude, this compound may be used in an amount representing from 0.0001% to 10% relative to the total weight of the composition, preferably in an amount representing from 0.0005% to 5% relative to the total weight of the composition and more preferably in an amount representing from 0.001% to 1% relative to the total weight of the composition.

The term "physiologically acceptable medium" means a medium that is compatible with the skin and possibly with its integuments (eyelashes, nails or hair) and/or mucous membranes.

The compositions according to the invention are suitable for topical application to the skin or for oral administration.

The composition of the invention may be in any conceivable presentation form suitable for topical application to the skin or for oral administration.

The composition of the invention may be for cosmetic or dermatological use. The composition of the invention is preferably for cosmetic use. Very preferably, the composition of the invention is a cosmetic composition for oral administration or for topical administration to the skin.

Some compositions of the invention may be cosmetic compositions because they are intended to maintain or improve the general appearance of the skin of an individual using it.

For oral administration, the composition may be in any suitable form, especially in the form of a drinkable solution, a syrup, a tablet, a gel capsule or a wafer capsule. The composition of the invention is preferably in the form of a gel capsule.

When it is intended for topical application to the skin, the composition may be in any presentation form normally used in cosmetics or dermatology, and it may especially be in the form of an optionally gelled aqueous solution, a dispersion of the lotion type, optionally a two-phase lotion, an emulsion obtained by dispersing a fatty phase in an aqueous phase (O/W emulsion) or conversely (W/O emulsion), or a triple emulsion (W/O/W or O/W/O emulsion) or a vesicular dispersion of ionic and/or nonionic type. These compositions are prepared according to the usual methods. A composition in the form of an oil-in-water emulsion is preferably used according to this invention.

This composition may be more or less fluid and may have the appearance of a white or coloured cream, an ointment, a milk, a lotion, a serum, a paste or a mousse. It may optionally be applied in the form of an aerosol. It may also be in solid form, in particular in the form of a stick. It may be used as a care product, and/or as a makeup product for the skin.

In a known manner, the composition used according to the invention may also contain adjuvants that are common in cosmetics, such as hydrophilic or lipophilic gelling agents, hydrophilic or lipophilic active agents, preserving agents, antioxidants, solvents, fragrances, fillers, UV-screening agents, pigments, odour absorbers and dyestuffs. The amounts of these various adjuvants are those conventionally used in the field under consideration, and, for example, from 0.01% to 20% relative to the total weight of the composition. Depending on their nature, these adjuvants may be introduced into the fatty phase, into the aqueous phase, or into lipid vesicles. In any case, these adjuvants, and also the proportions thereof, will be chosen so as not to harm the desired properties of the compounds of formula (I) according to the invention.

When the composition used according to the invention is an emulsion, the proportion of the fatty phase may range from 5% to 80% by weight and preferably from 5% to 50% by weight relative to the total weight of the composition. The oils, emulsifiers and co-emulsifiers used in the composition in emulsion form are chosen from those conventionally used in the field under consideration. The emulsifier and co-emulsifier are present in the composition in a proportion ranging from 0.3% to 30% by weight and preferably from 0.5% to 20% by weight relative to the total weight of the composition.

As oils that may be used in the invention, mention may be made of mineral oils (liquid petroleum jelly), oils of plant origin (avocado oil or soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax or ozokerite) may also be used as fatty substances.

As examples of emulsifiers and co-emulsifiers that may be used in the invention, mention may be made of fatty acid esters of polyethylene glycol such as PEG-100 stearate, and fatty acid esters of glycerol such as glyceryl stearate, or mixtures thereof.

Hydrophilic gelling agents that may be mentioned in particular include carboxyvinyl polymers (carbomer), acrylic copolymers such as acrylate/alkylacrylate copolymers, polyacrylamides, polysaccharides, natural gums and clays, and lipophilic gelling agents that may be mentioned include modified clays, for instance bentones, metal salts of fatty acids, hydrophobic silica and polyethylenes.

UV-screening agents that may be mentioned include benzylidenecamphor derivatives and benzotriazole derivatives.

The benzylidenecamphor derivatives are advantageously chosen from:

3-Benzylidenecamphor manufactured under the name "Mexoryl SD" by Chimex,

4-Methylbenzylidenecamphor sold under the name "Eusolex 6300" by Merck,

Camphorbenzalkonium methosulphate manufactured under the name "Mexoryl SO" by Chimex, Polyacrylamidomethylbenzylidenecamphor manufactured under the name "Mexoryl SW" by Chimex, sulphonic compounds such as:

Benzylidenecamphorsulphonic acid manufactured under the name "Mexoryl SL" by Chimex, and more particularly benzene-1,4-bis-(3-methylidene-10-camphorsulphonic acid) also known as Terephthalylidenedicamphorsulphonic acid manufactured under the name "Mexoryl SX" by Chimex, and its various salts described especially in patent applications FR-A-2 528 420 and FR-A-2 639 347, which are screening agents that are already known per se ("broad band" screening agents), capable specifically of absorbing ultraviolet radiation with wavelengths of between 280 and 400 nm, with absorption maxima of between 320 and 400 nm, in particular about 345 nm. These screening agents correspond to the general formula (III) below:

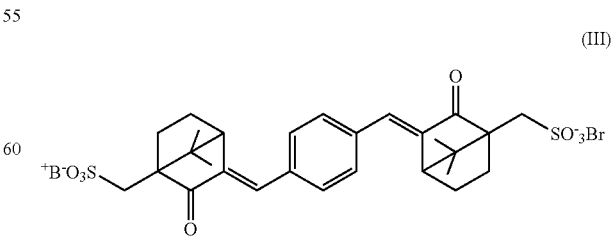

in which B denotes a hydrogen atom, an alkali metal or a radical $NH(R)_3^+$ in which the radicals R, which may be identical or different, denote a hydrogen atom, a $C_1$–$C_4$ alkyl or hydroxyalkyl radical or a group $M^{n+}/p$, $M^{n+}$ denoting a multivalent metal cation in which p is equal to 2, 3 or 4, $M^{n+}$ preferably denoting a metal cation chosen from $Ca^{2+}$, $Zn^{2+}$, $Mg^{2+}$, $Ba^{2+}$, $Al^{3+}$ and $Zr^{4+}$. It is clearly understood that the compounds of formula (III) above can give rise to the "cis-trans" isomer around one or more double bond(s) and that all the isomers fall within the context of the present invention.

Among the benzotriazole derivatives that may be mentioned are the silica derivatives described in patents EP 0 660 701 and EP 0 392 883. They are in particular silanes and/or polyorganosiloxanes containing a benzotriazole function comprising at least one unit of formula (1) below:

in which:

$R_7$ represents an optionally halogenated $C_1$–$C_{10}$ alkyl radical, a phenyl radical or a trimethylsilyloxy radical, a is an integer chosen between 0 and 3 inclusive, and the symbol G denotes a monovalent radical linked directly to a silicon atom, and which corresponds to formula (2) below:

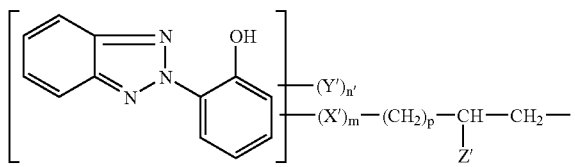

in which:

Y', which may be identical or different, are chosen from $C_1$–$C_8$ alkyl radicals, halogens and $C_1$–$C_4$ alkoxy radicals, it being understood that, in the latter case, two adjacent groups Y' on the same aromatic nucleus can together form an alkylidenedioxy group in which the alkylidene group contains 1 or 2 carbon atoms, X' represents O or NH, Z' represents hydrogen or a $C_1$–$C_4$ alkyl radical, n' is an integer between 0 and 3 inclusive, m is 0 or 1, p represents an integer between 1 and 10 inclusive.

Advantageously, the silicon derivative containing a benzotriazole function corresponds to formula (5) or (6) below:

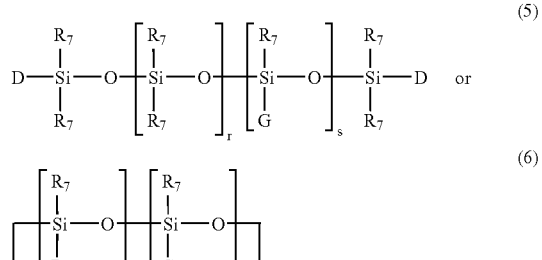

in which:

$R_7$, which may be identical or different, are chosen from $C_1$–$C_{10}$ alkyl, phenyl, 3,3,3-trifluoropropyl and trimethylsilyloxy radicals, at least 80%, in numerical terms, of the radicals $R_7$ being methyl, D, which may be identical or different, are chosen from the radicals $R_7$ and the radical G, r is an integer between 0 and 50 inclusive, and s is an integer between 0 and 20 inclusive, and, if s=0, at least one of the two symbols D denotes G, u is an integer between 1 and 6 inclusive, and t is an integer between 0 and 10 inclusive, it being understood that t+u is greater than or equal to 3, and the symbol G corresponds to formula (2) above.

One family of silicon derivatives containing a benzotriazole function that is preferred corresponds to formula (7) below:

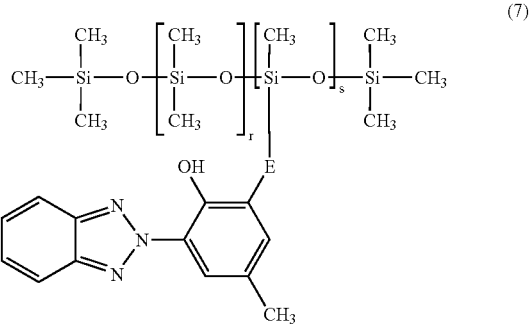

with $0 \leq r \leq 10$ $1 \leq s \leq 10$, and in which E represents the divalent radical:

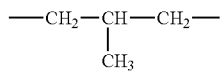

In a particularly preferred manner, the silicon derivative containing a benzotriazole function is Drometrizole Trisiloxane, which has the following formula (8):

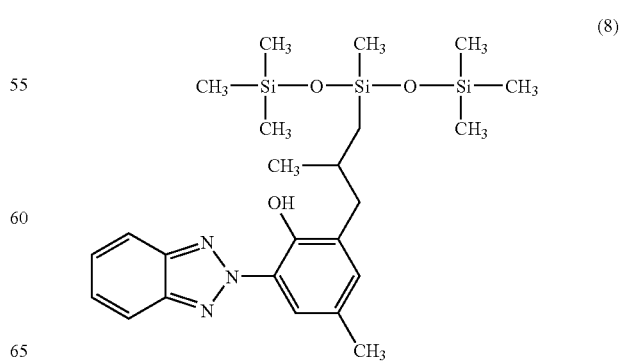

This compound is sold especially under the name "Silatrizole" by Rhodia Chimie.

The UV-screening agents are generally present in the compositions according to the invention in proportions ranging from 0.1% to 20% by weight relative to the total weight of the composition, and preferably ranging from 0.2% to 15% by weight relative to the total weight of the composition.

As active agents, it will be advantageous to introduce into the composition used according to the invention at least one compound chosen from: moisturizers; depigmenting or propigmenting agents; anti-pollution agents and/or free-radical scavengers; antimicrobial agents; NO-synthase inhibitors; agents for stimulating the synthesis of dermal or epidermal macromolecules and/or for preventing their degradation; agents for stimulating the proliferation of fibroblasts and/or keratinocytes or for stimulating keratinocyte differentiation; dermo-decontracting agents; tensioning agents; calmatives; agents acting on the capillary circulation; agents acting on the energy metabolism of cells; and mixtures thereof.

Examples of such additional compounds are given below.

1. Moisturizers

The term "moisturizer" means:

either a compound acting on the barrier function, in order to maintain the moisturization of the stratum corneum, or an occlusive compound. Mention may be made of ceramides, sphingoid-based compounds, lecithins, glycosphingolipids, phospholipids, cholesterol and its derivatives, phytosterols (stigmasterol, β-sitosterol or campesterol), essential fatty acids, 1,2-diacylglycerol, 4-chromanone, pentacyclic triterpenes such as ursolic acid, petroleum jelly and lanolin;

or a compound that directly increases the water content of the stratum corneum, such as threalose and its derivatives, hyaluronic acid and its derivatives, glycerol, pentanediol, sodium pidolate, serine, xylitol, sodium lactate, polyglyceryl acrylate, ectoin and its derivatives, chitosan, oligosaccharides and polysaccharides, cyclic carbonates, N-lauroylpyrrolidonecarboxylic acid and N-α-benzoyl-L-arginine;

or a compound that activates the sebaceous glands, such as steroid derivatives (such as DHEA, its 7-oxide and 17-alkyl derivatives and sapogenins) and vitamin D and its derivatives.

These compounds may represent from 0.001% to 30% and preferably from 0.01% to 20% relative to the total weight of the composition according to the invention.

The composition according to the present invention comprising the moisturizers mentioned above is advantageously intended for preventing or treating dryness of the skin and especially xerosis.

2. Depigmenting or Propigmenting Agent

The depigmenting agents that may be incorporated into the composition according to the present invention comprise, for example, the following compounds: kojic acid; ellagic acid; arbutin and its derivatives such as those described in patent applications EP-895 779 and EP-524 109; hydroquinone; aminophenol derivatives such as those described in patent applications WO 99/10318 and WO 99/32077, and in particular N-cholesteryloxycarbonyl-para-aminophenol and N-ethyloxycarbonyl-para-aminophenol; iminophenol derivatives, in particular those described in patent application WO 99/22707; L-2-oxothiazolidine-4-carboxylic acid or procysteine, and also its salts and esters; ascorbic acid and its derivatives, especially ascorbyl glucoside; and plant extracts, in particular extracts of liquorice, of mulberry and of skullcap, without this list being limiting.

Propigmenting agents that may be mentioned include the extract of burnet (*Sanguisorba officinalis*) sold by the company Maruzen, and extracts of chrysanthemum (*Chrysanthemum morifolium*).

The composition according to the present invention comprising the depigmenting agents mentioned above is advantageously intended for preventing or treating hyperpigmentation, in particular pigmentation marks associated with ageing of the skin.

For its part, the composition containing the propigmenting agents mentioned above is preferably intended for treating baldness.

3. Antimicrobial Agents

The antimicrobial agents that may be used in the composition according to the invention may be chosen especially from 2,4,4'-trichloro-2'-hydroxydiphenyl ether (or triclosan), 3,4,4'-trichlorobanilide, phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanilide, octopirox, octoxyglycerine, octanoylglycine, caprylyl glycol, 10-hydroxy-2-decanoic acid, dichlorophenyl imidazole dioxolane and its derivatives, described in patent WO 93/18743, farnesol and phytosphingosines, and mixtures thereof.

The preferred antibacterial agents are triclosan, phenoxyethanol, octoxyglycerine, octanoylglycine, 10-hydroxy-2-decanoic acid, caprylyl glycol, farnesol and azelaic acid.

By way of example, the antimicrobial agent may be used in the composition according to the invention in an amount representing from 0.1% to 20% and preferably from 0.1% to 10% relative to the total weight of the composition.

The composition containing the antimicrobial agent is particularly suitable for use in treating acne-prone greasy skin, acne or scalp dandruff.

4. Anti-Pollution Agent or Free-Radical Scavenger

The term "anti-pollution agent" means any compound capable of trapping ozone, monocyclic or polycyclic aromatic compounds such as benzopyrene and/or heavy metals such as cobalt, mercury, cadmium and/or nickel. The term "free-radical scavenger" means any compound capable of trapping free radicals.

As ozone-trapping agents that may be used in the composition according to the invention, mention may be made in particular of vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chlorogenic acid; stilbenes, in particular resveratrol; sulphur-containing amino acid derivatives, in particular S-carboxymethylcysteine; ergothioneine; N-acetylcysteine; chelating agents, for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenylalanine, tyrosine and hydrolysed RNA, sold by the Laboratoires Serobiologiques under the trade name CPP LS 2633-12F®, the water-soluble fraction of corn sold by the company Solabia under the trade name Phytovityl®, the mixture of extract of fumitory and of extract of lemon sold under the name Unicotrozon C-49® by the company Induchem, and the mixture of extracts of ginseng, of apple, of peach, of wheat and of barley, sold by the company Provital under the trade name Pronalen Bioprotect®.

As agents for trapping monocyclic or polycyclic aromatic compounds, which may be used in the composition according to the invention, mention may be made in particular of tannins such as ellagic acid; indole derivatives, in particular 3-indolecarbinol; extracts of tea, in particular of green tea, extracts of water hyacinth or *Eichhornia crassipes*; and the water-soluble fraction of corn sold by the company Solabia under the trade name Phytovityl®.

Finally, as heavy-metal-trapping agents that may be used in the composition according to the invention, mention may be made in particular of chelating agents such as EDTA, the pentasodium salt of ethylenediaminetetra-methylenephosphonic acid, and N,N'-bis(3,4,5-trimethoxybenzyl)ethylenediamine or one of the salts, metal complexes or esters thereof; phytic acid; chitosan derivatives; extracts of tea, in particular of green tea; tannins such as ellagic acid; sulphur-containing amino acids such as cysteine; extracts of water hyacinth (*Eichhornia crassipes*); and the water-soluble fraction of corn sold by the company Solabia under the trade name Phytovityl®.

The free-radical scavengers that may be used in the composition according to the invention comprise, besides certain anti-pollution agents mentioned above, vitamin E and its derivatives such as tocopheryl acetate; bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted naphthalenones; pidolates; phytanetriol; gamma-oryzanol; lignans; and melatonin.

5. NO-Synthase Inhibitor

Examples of NO-synthase inhibitors that are suitable for use in the present invention especially comprise an extract of a plant of the species *Vitis vinifera* which is sold especially by the company Euromed under the name Leucocyanidines de raisins extra, or by the company Indena under the name Leucoselect®, or finally by the company Hansen under the name Extrait de marc de raisin; an extract of a plant of the species *Olea europaea* which is preferably obtained from olive tree leaves and is sold especially by the company Vinyals in the form of a dry extract, or by the company Biologia & Technologia under the trade name Eurol BT; and an extract of a plant of the species *Gingko biloba* which is preferably a dry aqueous extract of this plant sold by the company Beaufour under the trade name *Gingko biloba* extrait standard.

The composition according to the invention comprising an NO-synthane inhibitor as defined above can advantageously be used to present or treat signs of ageing of the skin and/or sensitive skin.

6. Agent for Stimulating the Synthesis of Dermal or Epidermal Macromolecules and/or for Preventing their Degradation Among the active agents for stimulating dermal macromolecules or for preventing their degradation, mention may be made of those that act:

either on collagen synthesis, such as extracts of *Centella asiatica*; asiaticosides and derivatives; ascorbic acid or vitamin C and its derivatives; synthetic peptides such as lamin, biopeptide CL or the palmitoyloligopeptide sold by the company Sederma; peptides extracted from plants, such as the soybean hydrolysate sold by the company Coletica under the trade name Phytokine®; and plant hormones such as auxins and lignans;

or on elastin synthesis, such as the extract of *Saccharomyces cerivisiae* sold by the company LSN under the trade name Cytovitin®; and the extract of the alga *Macrocystis pyrifera* sold by the company Secma under the trade name Kelpadelie®;

or on glycosaminoglycan synthesis, such as the product of fermentation of milk with *Lactobacillus vulgaris*, sold by the company Brooks under the trade name Biomin yogourth®; the extract of the brown alga *Padina pavonica* sold by the company Alban Müller under the trade name HSP3; and the extract of *Saccharomyces cerevisiae* available especially from the company Silab under the trade name Firmalift® or from the company LSN under the trade name Cytovitin®;

or on fibronectin synthesis, such as the extract of the zooplankton Salina sold by the company Seporga under the trade name GP4G®; the yeast extract available especially from the company Alban Müller under the trade name Drieline®; and the palmitoyl pentapeptide sold by the company Sederma under the trade name Matrixil®;

or on the inhibition of metalloproteases (MMPs), such as, more particularly, MMP 1, 2, 3 or 9. Mention may be made of: retinoids and derivatives, oligopeptides and lipopeptides, lipoamino acids, the malt extract sold by the company Coletica under the trade name Collalift®; extracts of blueberry or of rosemary; lycopene; isoflavones, their derivatives or plant extracts containing them, in particular extracts of soybean (sold, for example, by the company Ichimaru Pharcos under the trade name Flavosterone SB®), of red clover, of flax, of kakkon, or of sage;

or on the inhibition of serine proteases such as leukocyte elastase or cathepsin G. Mention may be made of: the peptide extract of *Leguminosa* seeds (*Pisum sativum*) sold by the company LSN under the trade name Parelastyl®; heparinoids; and pseudodipeptides such as {2-[acetyl-(3-trifluoromethylphenyl)amino]-3-methylbutynylamino}acetic acid.

Among the active agents that stimulate epidermal macromolecules, such as fillagrin and keratins, mention may be made especially of the extract of lupin sold by the company Silab under the trade name Structurine®; the extract of beech *Fagus sylvatica* buds sold by the company Gattefosse under the trade name Gatuline®; and the extract of the zooplankton Salina sold by the company Seporga under the trade name GP4G®.

The composition according to the invention containing one or more of the above compounds is particularly suitable for use in preventing or treating signs of ageing of the skin, in particular of loss of firmness and/or of elasticity of the skin.

7. Agent for Stimulating the Proliferation of Fibroblasts or Keratinocytes and/or Keratinocyte Differentiation The agents for stimulating the proliferation of fibroblasts that may be used in the composition according to the invention may be chosen, for example, from plant proteins or polypeptides, extracts, especially of soybean (for example an extract of soybean sold by the company LSN under the name Eleseryl SH-VEG 8 or sold by the company Silab under the trade name Raffermine®); and plant hormones such as giberrellins and cytokinins.

The agents for stimulating the proliferation of keratinocytes that may be used in the composition according to the invention especially comprise retinoids such as retinol and its esters, including retinyl palmitate; phloroglucinol; extracts of nut cakes sold by the company Gattefosse; and extracts of *Solanum tuberosum* sold by the company Sederma.

The agents for stimulating keratinocyte differentiation comprise, for example, minerals such as calcium; the extract of lupin sold by the company Silab under the trade name Photopreventine®; sodium beta-sitosteryl sulphate sold by the company Seporga under the trade name Phytocohesine®; and the extract of corn sold by the company Solabia under the trade name Phytovityl®; and lignans such as secoisolariciresinol.

The composition according to the invention comprising these compounds is preferably intended to be used for preventing or treating signs of ageing of the skin.

8. Dermo-Decontracting Agent

The dermo-decontracting agents that may be used in the composition according to the invention comprise alverine and its salts, manganese gluconate, Diazepam, the hexapeptide argireline R sold by the company Lipotec, certain carbonylated secondary and tertiary amines, adenosine, and also sapogenines and the natural extracts, in particular of Wild Yam, containing them.

The composition according to the invention comprising these compounds is preferably intended to be used for preventing or treating signs of ageing of the skin, and in particular wrinkles.

9. Tensioning Agent

The term "tensioning agent" means a compound capable of exerting tension on the skin, the effect of which is to temporarily fade out irregularities on the skin's surface, such as wrinkles and fine lines.

Among the tensioning agents that may be used in the composition according to the present invention, mention may be made especially of:

(1) synthetic polymers, such as polyurethane latices or acrylic-silicone latices, in particular those described in patent application EP-1 038 519, such as a propylthio (polymethyl acrylate), propylthio(polymethyl methacrylate) and propylthio(polymethacrylic acid) grafted polydimethylsiloxane, or alternatively a propylthio(polyisobutyl methacrylate) and propylthio(polymethacrylic acid) grafted polydimethylsiloxane. Such grafted silicone polymers are sold especially by the company 3M under the trade names VS 80, VS 70 or LO21.

(2) polymers of natural origin, especially (a) polyholosides, for example (i) in the form of starch derived especially from rice, corn, potato, cassaya, pea, *Triticum aestivum* wheat, oat, etc. or (ii) in the form of carrageenans, alginates, agars, gelans, cellulose-based polymers and pectins, advantageously as an aqueous dispersion of gel microparticles, and (b) latices consisting of shellac resin, sandarac gum, dammar resins, elemi gums, copal resins and cellulose-based derivatives, and mixtures thereof, (3) plant proteins and protein hydrolysates, in particular from corn, rye, *Triticum aestivum* wheat, buckwheat, sesame, spelt, pea, bean, lentil, soybean and lupin, (3) mixed silicates, especially phyllosilicates and in particular Laponites, (4) wax microparticles chosen, for example, from carnauba wax, candelilla wax and alfalfa wax, (5) colloidal particles of mineral filler with a number-average diameter of between 0.1 and 100 nm and preferably between 3 and 30 nm, chosen, for example, from: silica, silic-alumina composites, cerium oxide, zirconium oxide, alumina, calcium carbonate, barium sulphate, calcium sulphate, zinc oxide and titanium dioxide.

The compositions according to the invention comprising the above tensioning agents are advantageously intended for treating signs of ageing of the skin, in particular wrinkles and fine lines.

10. Calmatives

As calmatives that may be used in the composition according to the invention, mention may be made of: pentacyclic triterpenes and extracts of plants (e.g.: *Glycyrrhiza glabra*) containing them, for instance β-glycyrrhetinic acid and salts and/or derivatives thereof (glycyrrhetinic acid monoglucoronide, stearyl glycyrrhetinate or 3-stearoyloxyglycyrrhetic acid), ursolic acid and its salts, oleanolic acid and its salts, betulinic acid and its salts, an extract of *Paeonia suffruticosa* and/or *lactiflora*, salicylic acid salts and in particular zinc salicylate, the phycosaccharides from the company Codif, an extract of *Laminaria saccharina*, canola oil, bisabolol and camomile extracts, allantoin, Sepivital EPC (phosphoric diester of vitamins E and C) from SEPPIC, omega-3 unsaturated oils such as musk rose oil, blackcurrant oil, ecchium oil, fish oil, plankton extracts, capryloylglycine, Seppicalm VG (sodium palmitoylproline and *Nymphea alba*) from SEPPIC, an extract of *Pygeum*, an extract of *Boswellia serrata*, an extract of *Centipeda cunnighami*, an extract of *Helianthus annuus*, an extract of *Linum usitatissimum*, tocotrienols, extracts of *Cola nitida*, piperonal, an extract of clove, an extract of *Epilobium angustifolium, Aloe vera*, an extract of *Bacopa moniera*, phytosterols, cortisone, hydrocortisone, indomethacin and betamethasone.

11. Agents Acting on the Capillary Circulation

The active agents acting on the capillary circulation (vasoprotective or vasodilating agents) may be chosen from flavonoids, ruscogenins, esculosides, escin extracted from common horse chestnut, nicotinates, heperidine methyl chalcone, essential oils of lavender or of rosemary, and extracts of *Ammi visnaga*.

The amount of these active agents may vary within a wide range. In general, these active agents are present in a concentration ranging from 0.01% to 15% and preferably from 0.05% to 10% by weight relative to the total weight of the composition.

12. Agents Acting on the Energy Metabolism of Cells

The active agents concerned are those acting on the energy metabolism of the skin, for instance, and in a non-limiting manner, ATP synthesis, and also those involved in the respiratory chain of the cell or in the energy reserves. Mention may be made of coenzyme Q10 (ubiquinone), cytochrome C, creatine or phosphocreatine.

A subject of the invention is also a cosmetic process for treating the skin via the oral administration or the topical application to the skin of a cosmetic composition as defined above, to maintain or improve the general appearance of the skin of an individual using it.

The invention is illustrated in greater detail in the examples that follow. These examples cannot in any way limit the scope of the invention.

EXAMPLE 1

General Process for Synthesizing the Derivatives of Formula (I)

First Step with an Amino Acid or a Hydroxy Acid as Starting Material

After drying under vacuum-nitrogen and under nitrogen, 4 g of L-2-oxothiazolidine-4-carboxylic acid (supplier: Aldrich) (0.0271 mol, 1 equivalent) are placed in a 500 mL three-necked flask. 200 mL of anhydrous acetonitrile are added and the mixture is heated until dissolution is complete. 3.15 g of 98% N-hydroxysuccinimide (NHS, 0.0271 mol, 1 equivalent) are added in a single portion. The mixture is cooled to 0° C., followed by dropwise addition of a solution of 5.61 g of 98% dicyclohexylcarbodiimide (DCC, 0.0271 mol, 1 equivalent) dissolved in 70 mL of anhydrous acetonitrile.

The mixture is stirred at 0° C. for one hour and then at room temperature for one hour. 1 equivalent of tert-butyl ester of amino acid hydrochloride or of tert-butyl ester of hydroxy acid is added in a single portion along with 7.58 mL of triethylamine (TEA, 0.0544 mol, 2 equivalents). When the tert-butyl ester of the amino acid or of the hydroxy acid is not a hydrochloride, only one equivalent of triethylamine is used.

The mixture is stirred for 15 hours.

The white precipitate obtained is filtered off and the filtrate is evaporated under reduced pressure (pressure of 200 mbar, temperature of 40° C.). The oil obtained is taken up in 200 mL of ethyl acetate (or dichloromethane) and washed with 3×100 mL of water and 100 mL of saturated sodium chloride solution. The organic phase is dried over sodium sulphate, filtered and evaporated under reduced pressure (p=220 mbar, T=40° C.)

The pure product is obtained by column chromatography (silica gel 60, 0.04–0.063 mm), eluent: 98/2 dichloromethane/methanol.

First Step with a Halo Acid as Starting Material

A solution of 20 mmol of L-2-oxothiazolidine-4-carboxylic acid and of 10.2 mmol of $K_2CO_3$ dissolved in DMF is brought to 80° C. and 22.4 mmol of halo acid (protected in tert-butyl ester form) are added. The reaction medium is stirred at 80° C. for 3 hours. After cooling to room temperature, the reaction medium is diluted with 300 mL of ethyl acetate and then washed 3 times with 100 mL of water and then once more with 10 mL of saturated NaCl solution. The organic phase is dried over $Na_2SO_4$, filtered and then concentrated under reduced pressure (p=220 mbar, T=40° C.).

Second Step 1 equivalent of the product obtained from the first step (0.01764 mol, 1 equivalent) in 65 mL of 1,2-dichloroethane is placed in a 100 mL three-necked flask. 6.75 mL of trifluoroacetic acid (TFA, 0.0882 mol, 5 equivalents) and 2.82 mL of triethylsilane (0.01764 mol, 1 equivalent) are added. The mixture is heated at 50° C. for 15 hours.

The 1,2-dichloroethane is evaporated off under reduced pressure (p=200 mbar, T=40° C.).

Work-Up:

a) If the compound is lipophilic: the oil obtained is taken up in 100 mL of ethyl acetate, extracted with 2×50 mL of saturated sodium hydrogen carbonate solution and then with 2×50 mL of water. The aqueous phase is acidified to pH=2 with 6N hydrochloric acid solution and then extracted with 6×100 mL of ethyl acetate. The combined organic phases are dried over sodium sulphate, filtered and then evaporated under reduced pressure (p=220 mbar, 40° C.).

b) If the compound is hydrophilic: the oil obtained is taken up in 100 mL of water and washed with 2×40 mL of dichloromethane and then freeze-dried (p=$10^{-2}$ mbar, T=−50° C.).

Third Step

After drying under vacuum-argon, 1 equivalent of the product obtained from the second step (0.01385 mol) are placed in 100 mL of anhydrous acetonitrile in a 500 mL three-necked flask. 1.606 g of 98% N-hydroxysuccinimide (NHS, 0.01385 mol, 1 equivalent) and 2.657 g of 1-(3-dimethylaminopropyl)- 3-ethylcarbodiimide hydrochloride (EDCI, 0.01385 mol, 1 equivalent) are added. The mixture is stirred at room temperature for 2 hours. The solution is diluted with 400 mL of anhydrous acetonitrile, 1.93 mL of triethylamine (TEA, 0.01385 mol, 1 equivalent) are added and the resulting mixture is stirred for 3 hours at room temperature.

The reaction mixture is evaporated under reduced pressure (p=200 mbar).

Work-Up:

a) Case of the Water-Stable Derivatives:

The evaporated crude product is taken up in 100 mL of dichloromethane and washed with 3×20 mL of water. The organic phase is dried over sodium sulphate, filtered and evaporated under reduced pressure (p=950 mbar, T=40° C.). A white solid is obtained, which is taken up in 8 mL of acetone. The precipitate is filtered off and washed with 3×2 mL of acetone. This operation is repeated twice (total removal of N-hydroxysuccinimide). The pure product is obtained after drying under reduced pressure (p=$10^{-1}$ mbar, room temperature).

b) Case of the Water-Unstable Derivatives

The evaporated crude product is purified by column chromatography (personal flash master, BP SUP column), eluent: 8/2 cyclohexane/acetone. The solid obtained is taken up in 2 mL of acetone. Diethyl ether is added gradually until precipitation occurs. The pure product is isolated by precipitation after drying under reduced pressure (p=$10^{-1}$ mbar, room temperature).

EXAMPLE 2

Compounds Obtained According to the Synthetic Process of Example 1

Compound 1: 6-Phenyltetrahydrothiazolo[3,4-a] pyrazine-3,5,8-trione

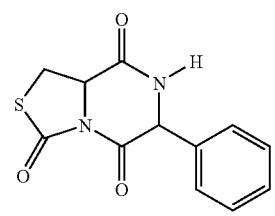

Mixture of diastereoisomers A/B: 5/1

$^1$H NMR (400 MHz; DMSO) δ ppm 3.58 (m, 4H); 4.93 (dd, 1H, J=10.98 Hz and 7.69 Hz, A); 5.14 (dd, 1H, J=10.43 Hz and 8.23 Hz, B); 5.21 (s, 1H, A); 5.37 (s, 1H, B); 7.40 (m, 10H); 8.86 (s, 1H, B); 9.18 (s, 1H, A).

The mass of the product is confirmed by the following mass spectrum:

MS: m/z=285 (M+Na, 100%), 261 (MH−, 100%).

Compound 2: Tetrahydrothiazolo[3,4-a]pyrazine-3,5,8-trione

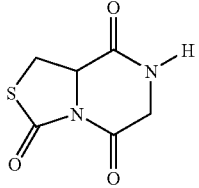

¹H NMR (400 MHz; DMSO) δ ppm: 3.53 (d, 2H, H7, J=9.51 Hz); 3.72 (dd, 1H, H4, J=4.66 and 17.2 Hz); 4.17 (d, 1H, H4, J=17.2 Hz); 5.00 (t, 1H, H6a, J=9.51 Hz); 8.52 (s, 1H, NH).

The mass of the product is confirmed by the following mass spectrum:

MS: m/z=186.91 (MH+, 10%), 208.91 (M+Na, 6%), 185.08 (M−, 2%).

Compound 3: 6-Benzyltetrahydrothiazolo[3,4-a]pyrazine-3,5,8-trione

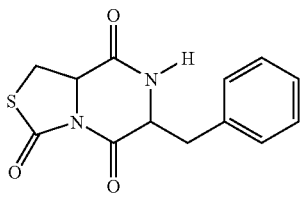

¹H NMR (400 MHz; DMSO) δ ppm: 3.01 (dd, 1H, H1', J=5.49 and 13.54 Hz), 3.14 (dd, 1H, H', J=6.86 and 13.72 Hz); 3.40 (m, 2H, H7); 4.06 (dd, 1H, H6a, J=10.98 and 7.68 Hz); 4.19 (dd, 1H, H4, J=10.71 and 5.58 Hz); 7.20 (m, 2H, C6H5); 7.33 (m, 3H, C6H5); 8.57 (s, 1H, NH).

The mass of the product is confirmed by the following mass spectrum:

MS: m/z=276.98 (MH+, 14%), 298.95 (M+Na, 100%), 275.03 (M−, 100%).

Compound 4: Hexahydropyrrolo[1,2-a]thiazolo[3,4-d]pyrazine-3,5,10-trione

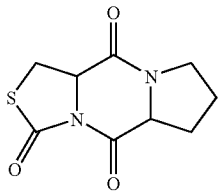

¹H NMR (400 MHz; DMSO) δ ppm: 1.87 (m, 2H, H5); 2.05 (m, 1H, H4); 2.18 (m, 1H, H4); 3.41 (m, 2H, H6); 3.54 (dd, 2H, H8, J=4.02 and 9.33 Hz); 4.49 (t, 1H, H3a, J=7.96 Hz); 5.13 (t, 1H, H7a, J=9.24 Hz).

The mass of the product is confirmed by the following spectrum:

MS: m/z=226.96 (MH+, 15%), 248.95 (M+Na, 100%), 225.00 (M−, 100%).

Compound 5: 1H-[1,3]thiazolo[4,3-c]oxazine-3,5,8-[6H,8aH]-trione

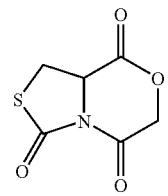

¹H NMR (400 MHz; DMSO) δ ppm 3.64 (m, 1H, H3a); 3.94 (m, 1H, H3b); 5.09 (d, 1H, H6a); 5.35 (m, 1H, H4); 5.53 (d, 1H, H6b) ¹³C NMR (400 MHz; DMSO) δ ppm 29.28 (C3); 57.49 (C4); 64.48 (C6); 164.98 (C7); 167.98 (C5); 172 (C1)

EXAMPLE 3

Method for Evaluating the Active Photo-Protection of the Derivatives of the Invention Against UVA Oxidative Stress Induced on Keratinocytes The photoprotection evaluation technique is performed according to a well-known method (J. of Photochemistry and Photobiology B: Biology 57 (2000) 102–112 TOBI et al: Glutathione modulates the level of free radicals produced in UVA irradiated cells). This technique uses a fluorescent probe, a marker of intracellular global oxidative stress, 2',7'-dichlorofluoresceine diacetate (DCFH-DA).

Principle

The use of DCFH-DA as an oxidative stress marker is based on its physicochemical properties. It is a nonionic apolar molecular capable of diffusing across cell membranes. Once inside the cell, DCFH-DA is hydrolysed by intracellular esterases to a non-fluorescent compound: DCFH or 2,7-dichlorofluoresceine. In the presence of activated oxygen species, DCFH is rapidly oxidized to a highly fluorescent compound: DCF or 2,7-dichlorofluoresceine.

Procedure

1. Treatment of Keratinocytes with a Compound of Formula (I).

At confluence, the keratinocytes are incubated in the presence of a compound of formula (I) for 24 hours at 37° C., 5% $CO_2$, in the culture medium, according to a dose effect (3 concentrations).

2. Incorporation of DCFH-DA

The keratinocytes, pretreated with a compound of formula (I), are rinsed and then incubated in the presence of DCFH-DA in the dark.

3. Exposure to UVA

After this incubation, the DCFH-DA solution is removed and the cells are then exposed to UVA.

Comment: a non-exposed control plate is stored in the dark, at room temperature.

4. Measurement of the Fluorescence

The fluorescence of the DCF is evaluated immediately after the exposure to UVA, via spectrofluorimetry (excitation: 480 nm; emission: 530 nm).

5. Results

The results are expressed as % of fluorescence relative to the control cells exposed to UVA:

| Compound 2 [mM] | TEST 1 | TEST 2 | Mean | Standard deviation |
|---|---|---|---|---|
| 0 | 100 | 100 | 100 | 0 |
| 0.05 | 98 | 86 | 92 | 8.5 |
| 0.5 | 79 | 74 | 76.5 | 3.5 |
| 5 | 69 | 58 | 63.5 | 7.8 |

The photoprotective effect of compound 2 was evaluated at 0.05, 0.5 and 5 mM.

The results reveal a protective efficacy of compound 2 with respect to UVA oxidative stress induced according to a dose effect: the optimum efficacy is obtained at 5 mM (reduction of fluorescence by about 36%).

It is clearly seen that the derivatives of formula (I) according to the invention induce active photoprotection of the skin compared with the untreated control.

EXAMPLE 4

Compositions 0.2 g lozenge obtained after compacting:

| Compound 1 | 0.001 g |
|---|---|
| Starch | 0.114 g |
| Calcium phosphate | 0.020 g |
| Lactose | 0.060 g |
| Magnesium stearate | 0.005 g |

The lozenges obtained are suitable for oral administration.

Oral Suspension

| Compound 1 | 0.001 g |
|---|---|
| Glycerol | 0.500 g |
| Sorbitol | 0.500 g |
| Sodium saccharinate | 0.010 g |
| Methyl para-hydroxybenzoate | 0.040 g |
| Flavouring | qs |
| made up to 5 mL with purified water | |

Facial Cream

| Compound 3 | 1.00% |
|---|---|
| Sodium stearate | 3.00% |
| Liquid petroleum jelly | 6.00% |
| Alkyl paraben | 0.05% |
| Potassium sorbate | 10.00% |
| Stearyl alcohol | 1.00% |
| Fragrance | 1.00% |
| Water qs | 100.00% |

Body Cream

| Compound 3 | 0.5% |
|---|---|
| Jojoba oil | 13.0% |
| Sipol wax | 6.0% |
| Isopropyl palmitate | 2.0% |
| Glycerol | 15.0% |
| Alkyl paraben | 0.5% |
| Fragrance | 1.0% |
| Water qs | 100.00% |

Antisun Care Cream

| Compound 3 | 1% |
|---|---|
| Oxyethylenated (50) polyethylene glycol | 3% |
| Mono-diglyceryl stearate | 3% |
| Liquid petroleum jelly | 24% |
| Cetyl alcohol | 5% |
| Water qs | 100.0% |

Antisun Bodycare Cream

| Compound 3 | 0.5% |
|---|---|
| Sipol wax | 6.0% |
| Glyceryl monostearate | 1.5% |
| Sodium stearate | 0.8% |
| Liquid petroleum jelly | 6.0% |
| Isopropyl palmitate | 2.0% |
| Glycerol | 15.0% |
| Fragrance | 0.3% |
| Water qs | 100.0% |

Care Cream

| Compound 3 | 0.1% |
|---|---|
| Jojoba oil | 13.00% |
| Alkyl paraben | 0.05% |
| Potassium sorbate | 0.30% |
| Cyclopentadimethylsiloxane | 10.00% |
| Stearyl alcohol | 1.00% |
| Stearic acid | 4.00% |
| Polyethylene glycol stearate | 3.00% |
| Vitamin E | 1.00% |
| Glycerol | 3.00% |
| Water qs | 100.00% |

Antisun Cream

| Cetearyl alcohol (and) Ceteareth-30 sold by the company Cognis under the name Sinnowax AO | 7% |
|---|---|
| Glyceryl stearate sold by Stéarinerie Dubois under the name Stéarate de glycérol 50/50 | 2% |
| Cetyl alcohol sold by the company Cognis under the name Lanette 16 | 1.5% |
| Dimethicone sold by the company Dow Corning under the name DC 200 Fluid 350 CS | 1.5% |
| Mineral oil sold by the company Esso under the name Marcol 82 | 15% |

-continued

| | |
|---|---|
| Drometrizole trisiloxane | 4% |
| sold by the company Chimex under the name Mexoryl XL | |
| Terephthalylidenedicamphorsulphonic acid | 1.5% |
| sold by the company Chimex under the name Mexoryl SX | |
| Triethanolamine | 0.26% |
| sold by the company BASF under the name Triethanolamine Care | |
| Glycerol | 20% |
| sold by the company Uniquema under the name Pricerine 9091 | |
| Compound 3 | 0.1% |
| 6-benzyltetrahydrothiazolo[3,4-a]pyrazine-3,5,8-trione | |
| Preserving agent | qs |
| Water | qs 100 g |

0.2 g lozenge obtained after compacting:

| | |
|---|---|
| Compound 2 | 0.001 g |
| Starch | 0.114 g |
| Calcium phosphate | 0.020 g |
| Lactose | 0.060 g |
| Magnesium stearate | 0.005 g |

The lozenges obtained are suitable for oral administration.

Oral Suspension

| | |
|---|---|
| Compound 2 | 0.001 g |
| Glycerol | 0.500 g |
| Sorbitol | 0.500 g |
| Sodium saccharinate | 0.010 g |
| Methyl para-hydroxybenzoate | 0.040 g |
| Flavouring | qs |
| made up to 5 mL with purified water | |

Facial Cream

| | |
|---|---|
| Compound 2 | 1.00% |
| Sodium stearate | 3.00% |
| Liquid petroleum jelly | 6.00% |
| Alkyl paraben | 0.05% |
| Potassium sorbate | 10.00% |
| Stearyl alcohol | 1.00% |
| Fragrance | 1.00% |
| Water qs | 100.00% |

Body Cream

| | |
|---|---|
| Compound 2 | 0.5% |
| Jojoba oil | 13.0% |
| Sipol wax | 6.0% |
| Isopropyl palmitate | 2.0% |
| Glycerol | 15.0% |
| Alkyl paraben | 0.5% |
| Fragrance | 1.0% |
| Water qs | 100.0% |

Antisun Care Cream

| | |
|---|---|
| Compound 2 | 1% |
| Oxyethylenated (50) polyethylene glycol | 3% |
| Mono-diglyceryl stearate | 3% |
| Liquid petroleum jelly | 24% |
| Cetyl alcohol | 5% |
| Water qs | 100% |

Antisun Bodycare Cream

| | |
|---|---|
| Compound 2 | 0.5% |
| Sipol wax | 6.0% |
| Glyceryl monostearate | 1.5% |
| Sodium stearate | 0.8% |
| Liquid petroleum jelly | 6.0% |
| Isopropyl palmitate | 2.0% |
| Glycerol | 15.0% |
| Fragrance | 0.3% |
| Water qs | 100.0% |

Care Cream

| | |
|---|---|
| Compound 2 | 0.1% |
| Jojoba oil | 13.00% |
| Alkyl paraben | 0.05% |
| Potassium sorbate | 0.30% |
| Cyclopentadimethylsiloxane | 10.00% |
| Stearyl alcohol | 1.00% |
| Stearic acid | 4.00% |
| Polyethylene glycol stearate | 3.00% |
| Vitamin E | 1.00% |
| Glycerol | 3.00% |
| Water qs | 100.00% |

Antisun Cream

| | |
|---|---|
| Cetearyl alcohol (and) Ceteareth-30 | 7% |
| sold by the company Cognis under the name Sinnowax AO | |
| Glyceryl stearate | 2% |
| sold by Stéarinerie Dubois under the name Stéarate de glycérol 50/50 | |
| Cetyl alcohol | 1.5% |
| sold by the company Cognis under the name Lanette 16 | |
| Dimethicone | 1.5% |
| sold by the company Dow Corning under the name DC 200 Fluid 350 CS | |
| Mineral oil | 15% |
| sold by the company Esso under the name Marcol 82 | |
| Drometrizole trisiloxane | 4% |
| sold by the company Chimex under the name Mexoryl XL | |
| Terephthalylidenedicamphorsulphonic acid | 1.5% |
| sold by the company Chimex under the name Mexoryl SX | |
| Triethanolamine | 0.26% |
| sold by the company BASF under the name Triethanolamine Care | |
| Glycerol | 20% |
| sold by the company Uniquema under the name Pricerine 9091 | |

| | |
|---|---|
| Compound 2 | 0.1% |
| tetrahydrothiazolo[3,4-a]pyrazine-3,5,8-trione | |
| Preserving agent | qs |
| Water | qs 100 g |

The invention claimed is:

1. A 2-oxothiazolidine-4-carboxylic acid derivative of formula (I):

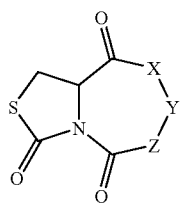

in which:
- X represents an oxygen atom or a radical NR";
- R" represents a linear, cyclic or branched alkyl radical containing from 1 to 12 carbon atoms, which is optionally substituted;
- Y represents a group $(CH_2)_n$;
- Z represents a group (CRR')
- n is an integer chosen from 0, 1, 2 and 3;
- R and R', which may be identical or different, represent:
  - a hydrogen atom;
  - an —Si—$(CH_3)_3$, —Si$(CH_3)_2$—OH, Si—$(CH_3)_2$—OEt, —Si—$(CH_3)_2$—O—$CH_2$—Ph or —Si—$(iPr)_2$—OEt radical;
  - a halogen;
  - an alkyl radical as defined above;
  - an optionally substituted aryl radical;
  - an optionally substituted arylalkyl radical;
- wherein when X represents a radical NR", R" and R' taken together can form, with the 2 atoms bearing them, a heterocycle containing 4, 5 or 6 carbon atoms; or wherein
  - Y and Z each represent a carbon atom and together form an aromatic heterocycle or ring containing 5, 6 or 7 carbon atoms, the said ring or heterocycle being optionally substituted; and
- the optical or geometrical isomers thereof, alone or as a mixture in all proportions, and the physiologically acceptable salts thereof.

2. The derivatives of claim 1, wherein n is chosen from 0 and 1.

3. The derivatives of claim 1 or 2, wherein R or R' is an aryl radical is a 5- or 6-membered aromatic ring or heterocycle, advantageously a phenyl radical.

4. The derivatives of either claim 1 or 2, wherein R or R' is an arylalkyl radical is a radical of 6 to 12 carbon atoms, in which the aryl portion is a 5- or 6-membered aromatic ring or heterocycle or a 5- or 6-membered aromatic heterocycle.

5. The derivatives of either claim 1 or 2, wherein R or R' is a substituted aryl radical or a substituted arylalkyl radical are substituted with at least one group chosen from a hydroxyl group (—OH), a cyano group (—CN), a trifluoromethyl group (—$CF_3$), a methoxy radical (—$OCH_3$) or a halogen atom chosen from chlorine, bromine, fluorine and iodine.

6. The derivatives of claim 1 or 2, wherein R or R' is a phenyl radical substituted with an alkyl radical, a hydroxyl group or a methoxy radical.

7. The derivatives of claim 1 or 2, wherein R or R' is a benzyl radical substituted with at least one group chosen from an alkyl radical, a hydroxyl group and a methoxy radical.

8. The derivatives of claim 6, wherein said phenyl radical is substituted with an alkyl radical which is of $C_1$–$C_4$.

9. The derivatives of claim 1 or 2, wherein:
- X represents an oxygen atom or a radical NR";
- Z represents a group (CRR') and n is equal to 0;
- R and R", which may be identical or different, represent a hydrogen atom, an alkyl radical as defined above or a cycloalkyl;
- R' represents a hydrogen atom, a phenyl radical, a benzyl radical or the side chain of an amino acid, preferably chosen from that of alanine, isoleucine, leucine, methionine, phenylalanine, tryptophan, valine, asparagine, cysteine, glutamine, glycine, serine, threonine, aspartic acid, glutamic acid, arginine, histidine and lysine; and
wherein R" and R taken together can form, with the two atoms bearing them, the side chain of proline, or
- Y and Z each represent a carbon atom and together form an optionally substituted aromatic ring containing 6 carbon atoms.

10. A 2-oxothiazolidine-4-carboxylic acid derivative selected from:
- tetrahydrothiazolo[3,4-a]pyrazine-3,5,8-trione;
- 6-methyltetrahydro[1,3]thiazolo[3,4-a]pyrazine-3,5,8-trione;
- 6-ethyltetrahydro[1,3]thiazolo[3,4-a]pyrazine-3,5,8-trione;
- 6-propyltetrahydro[1,3]thiazolo[3,4-a]pyrazine-3,5,8-trione;
- 6-iso-propyltetrahydro[1,3]thiazolo[3,4-a]pyrazine-3,5,8-trione;
- 6-propyltetrahydro[1,3]thiazolo[3,4-a]pyrazine-3,5,8-trione;
- 6-[1-methylpropyl]tetrahydro[1,3]thiazolo[3,4-a]pyrazine-3,5,8-trione;
- 6-isobutyltetrahydro[1,3]thiazolo[3,4-a]pyrazine-3,5,8-trione;
- 6-phenyltetrahydro[1,3]thiazolo[3,4-a]pyrazine-3,5,8-trione;
- 6-benzyltetrahydro[1,3]thiazolo[3,4-a]pyrazine-3,5,8-trione;
- 6-(methylsulphanyl)ethyltetrahydro[1,3]thiazolo[3,4-a]pyrazine-3,5,8-trione;
- 6-(ethylsulphanyl)methyltetrahydro[1,3]thiazolo[3,4-a]pyrazine-3,5,8-trione;
- 7-methyltetrahydrotetra[1,3]thiazolo[3,4-a]pyrazine-3,5,8-trione;
- 7-ethyltetrahydrotetra[1,3]thiazolo[3,4-a]pyrazine-3,5,8-trione;
- tetrahydro-1 H,5H-pyrrolo[1,2a][1,3]thiazolo[3,4d]pyrazine-3,5,10(10aH)trione;
- 3-(3,5,8-trioxohexahydrothiazolo[3,4-a]pyrazin-6-yl)propionic acid;
- 6-mercaptomethyltetrahydrothiazolo[3,4-a]pyrazine-3,5,8-trione;
- 7-methyltetrahydrothiazolo[3,4-a]pyrazine-3,5,8-trione;
- 6,7-dimethyltetrahydro[1,3]thiazolo[3,4-a]pyrazine-3,5,8-trione;
- 6-ethyl-7-methyltetrahydro[1,3]thiazolo[3,4-a]pyrazine-3,5,8-trione;

6-propyl-7-methyltetrahydro[1,3]thiazolo[3,4-a]pyrazine-3,5,8-trione;
6-iso-propyl-7-methyltetrahydro[1,3]thiazolo[3,4-a]pyrazine-3,5,8-trione;
6-propyl-7-methyltetrahydro[1,3]thiazolo[3,4-a]pyrazine-3,5,8-trione;
6-[1-methylpropyl]-7-methyltetrahydro[1,3]thiazolo[3,4-a]pyrazine-3,5,8-trione;
6-iso-butyl-7-methyltetrahydro[1,3]thiazolo[3,4-a]pyrazine-3,5,8-trione;
6-phenyl-7-methyltetrahydro[1,3]thiazolo[3,4-a]pyrazine-3,5,8-trione,
6-benzyl-7-methyltetrahydro[1,3]thiazolo[3,4-a]pyrazine-3,5,8-trione;
6-(methylsulphanyl)ethyl-7-methyltetrahydro[1,3]thiazolo[3,4-a]pyrazine-3,5,8-trione;
6-(ethylsulphanyl)methyl-7-methyltetrahydro[1,3]thiazolo[3,4-a]pyrazine-3,5,8-trione;
3-(3,5,8-trioxohexahydro-7-methylthiazolo[3,4-a]pyrazin-6-yl)propionic acid;
6-mercaptomethyl-7-methyltetrahydrothiazolo[3,4-a]pyrazine-3,5,8-trione;
1H-[1,3]thiazolo[4,3-c]oxazine-3,5,8-[6H,8aH]trione;
1,10a-dihydro-9-oxa-2-thia-3a-azabenzo[f]azulene-3,4,10-trione;
6-octanoyl-1,10a-dihydro-9-oxa-2-thia-3a-azabenzo[f]azulene-3,4,10-trione; and
(6-carboxymethyl-3,5,8-trioxotetrahydrothiazolo[4,3-c][1,4]oxazin-6-yl)acetic acid.

11. A process for manufacturing 2-oxothiazolidine-4-carboxylic acid derivatives of formula (I) from L-2-oxothiazolidine-4-carboxylic acid comprising the steps of:
i) a coupling reaction, in the presence of a base, between 2-oxothiazolidine-4-carboxylic acid and an amino acid, a hydroxy acid or a halo acid whose acid function is protected;
ii) a reaction of deprotection with an acidic agent of the protected acid function of the product obtained after step i);
iii) a intramolecular cyclization reaction of peptide type;
it being understood that step iii) is performed if the intramolecular cyclization does not take place spontaneously in step ii).

12. A composition comprising: in a physiologically acceptable medium, at least one derivative of formula (I) as defined in any one of claim 1, 2 or 10.

13. The composition according to claim 12, wherein said derivative of formula (I) represents from 0.0001% to 10% relative to the total weight of said composition.

14. The composition according to claim 12, further comprising at least one adjuvant chosen from hydrophilic or lipophilic gelling agents, hydrophilic or lipophilic active agents, preserving agents, antioxidants, solvents, fragrances, fillers, UV-screening agents, pigments, odour absorbers and dyestuffs.

15. The composition according to claim 14, wherein said UV-screening agents are chosen from benzylidenecamphor derivatives and benzotriazole derivatives.

16. The composition according to claim 15, wherein said benzylidenecamphor derivatives are chosen from:
3-Benzylidenecamphor;
4-Methylbenzylidenecamphor;
Camphorbenzalkonium methosulphate;
Polyacrylamidomethylbenzylidenecamphor;
sulphonic compounds such as:
Benzylidenecamphorsulphonic acid;
benzene-1,4-bis(3-methylidene-10-camphorsulphonic acid) and its various salts of general formula (III) below:

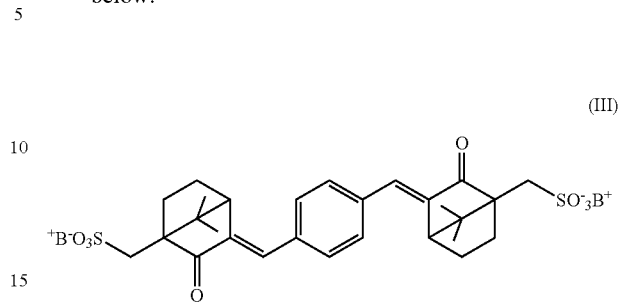

(III)

in which B denotes a hydrogen atom, an alkali metal or a radical $NH(R)_3^+$ in which the radicals R, which may be identical or different, denote a hydrogen atom, a $C_1$–$C_4$ alkyl or hydroxyalkyl radical or a group $M^{n+}/p$, $M^{n+}$ denoting a multivalent metal cation in which p is equal to 2, 3 or 4.

17. The composition according to claim 15, characterized in that the benzotriazole derivatives are silanes and/or polyorganosiloxanes containing a benzotriazole function comprising at least one unit of formula (1) below:

in which:
$R_7$ represents an optionally halogenated $C_1$–$C_{10}$ alkyl radical, a phenyl radical, or a trimethylsilyloxy radical,
a is an integer chosen between 0 and 3 inclusive, and
the symbol G denotes a monovalent radical linked directly to a silicon atom, and
which corresponds to formula (2) below:

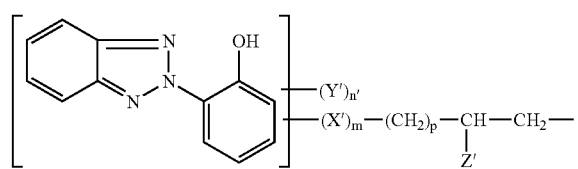

(2)

in which:
Y', which may be identical or different, are chosen from $C_1$–$C_8$ alkyl radicals, halogens and $C_1$–$C_4$ alkoxy radicals, it being understood that, in the latter case, two adjacent groups Y' on the same aromatic nucleus can together form an alkylidenedioxy group in which the alkylidene group contains 1 or 2 carbon atoms,
X' represents O or NH,
Z' represents hydrogen or a $C_1$–$C_4$ alkyl radical,
n' is an integer between 0 and 3 inclusive,
m is 0 or 1,
p represents an integer between 1 and 10 inclusive.

18. The composition according to claim 17, wherein said silane derivative containing a benzotriazole function corresponds to either formula (5) or (6) below:

(5)

$$D-\underset{R_7}{\overset{R_7}{Si}}-O-\left[\underset{R_7}{\overset{R_7}{Si}}-O\right]_r\left[\underset{G}{\overset{R_7}{Si}}-O\right]_s\underset{R_7}{\overset{R_7}{Si}}-D \quad \text{or}$$

(6)

$$\left[\underset{R_7}{\overset{R_7}{Si}}-O\right]_t\left[\underset{G}{\overset{R_7}{Si}}-O\right]_u$$

in which:
- $R_7$, which may be identical or different, are chosen from $C_1$–$C_{10}$ alkyl, phenyl, 3,3,3-trifluoropropyl and trimethylsilyloxy radicals, at least 80%, in numerical terms, of the radicals $R_7$ being methyl,
- D, which may be identical or different, are chosen from the radicals $R_7$ and the radical G,
- r is an integer between 0 and 50 inclusive, and s is an integer between 0 and 20 inclusive, and, if s=0, at least one of the two symbols D denotes G,
- u is an integer between 1 and 6 inclusive, and t is an integer between 0 and 10 inclusive, it being understood that t+u is greater than or equal to 3, and
- the symbol G corresponds to formula (2) defined in claim 17.

19. The composition according to claim 18, wherein said silane derivative containing a benzotriazole function corresponds to formula (7) below:

(7)

$$CH_3-\underset{CH_3}{\overset{CH_3}{Si}}-O\left[\underset{CH_3}{\overset{CH_3}{Si}}-O\right]_r\left[\underset{E}{\overset{CH_3}{Si}}-O\right]_s\underset{CH_3}{\overset{CH_3}{Si}}-CH_3$$

[benzotriazole-phenol-CH3 structure with OH]

with $0 \leq r \leq 10$ $1 \leq s \leq 10$, and in which E represents the divalent radical:

$$-CH_2-\underset{CH_3}{\overset{|}{CH}}-CH_2-$$

20. The composition according to claim 19, wherein said silane derivative containing a benzotriazole function is Drometrizole Trisiloxane, which has the following formula:

[Drometrizole Trisiloxane structure]

21. The composition according to claim 14, wherein said UV-screening agents are present in the composition in proportions ranging from 0.1% to 20% by weight relative to the total weight of the composition.

22. The composition according to claim 12, further comprising at least one compound chosen from moisturizers; depigmenting or propigmenting agents; anti-pollution agents and/or free-radical scavengers; antimicrobial agents; NO-synthase inhibitors; agents for stimulating the synthesis of dermal or epidermal macromolecules and/or for preventing their degradation; agents for stimulating the proliferation of fibroblasts and/or keratinocytes or for stimulating keratinocyte differentiation; dermo-decontracting agents; tensioning agents; calmatives; agents acting on the capillary circulation and/or agents acting on the energy metabolism of the cells; and mixtures thereof.

23. A method of treating skin to provide protection from UV-radiation comprising: applying to the skin a composition in accordance with claim 12.

24. A method of treating skin to provide protection from UV-radiation comprising: applying to the skin a composition in accordance with claim 13.

25. A method of treating skin to provide protection from UV-radiation comprising: orally administering to a patient in need of UV-protection a composition in accordance with claim 12.

26. A method of treating skin to provide protection from UV-radiation comprising: orally administering to a patient in need of UV-protection a composition in accordance with claim 13.

27. A method of improving the general appearance of the skin comprising administering topically or orally a composition according to claim 13 to a subject.

28. The derivative of claim 8, wherein said alkyl radical is selected from methyl, ethyl, propyl, isopropyl, butyl, isobutyl and tert-butyl radicals.

29. The derivative of claim 7, wherein said benzyl radical is substituted with an alkyl radical which is of $C_1$–$C_4$.

30. The derivative of claim 29 wherein said alkyl radical is selected from methyl, ethyl, propyl, isopropyl, butyl, isobutyl and tert-butyl radicals.

31. The composition according to claim 13, further comprising at least one adjuvant chosen from hydrophilic or lipophilic gelling agents, hydrophilic or lipophilic active agents, preserving agents, antioxidants, solvents, fragrances, fillers, UV-screening agents, pigments, odour absorbers and dyestuffs.

* * * * *

UNITED STATES PATENT AND TRADEMARK OFFICE
CERTIFICATE OF CORRECTION

| | | |
|---|---|---|
| PATENT NO. | : 7,022,317 B2 | Page 1 of 1 |
| APPLICATION NO. | : 10/830924 | |
| DATED | : April 4, 2006 | |
| INVENTOR(S) | : Irène Erdelmeier and Karine Lucet-Levannier | |

It is certified that error appears in the above-identified patent and that said Letters Patent is hereby corrected as shown below:

Column 10, line 60, "Br" should be -- B+ --.

Column 11, line 38, "are" should be -- is --.

Column 12, line 2, "are" should be -- is --.

Column 12, line 6, "are" should be -- is --.

Column 19, line 67, "are" should be -- is --.

Column 27, line 57, delete "is a radical"--.

Column 28, line 57, delete the space between tetrahydro-1 and H,5H-...

Column 29, line 41, "a" should be --an--.

Column 30, line 53, "are" should be --is--.

Column 31, line 18, "are" should be --is--.

Column 31, line 22, "are" should be --is--.

Signed and Sealed this

First Day of August, 2006

JON W. DUDAS
*Director of the United States Patent and Trademark Office*